United States Patent
Winkler et al.

(10) Patent No.: US 10,723,994 B2
(45) Date of Patent: Jul. 28, 2020

(54) DEVICE FOR SEPARATING ADULT STEM CELL

(71) Applicant: Human Med AG, Schwerin (DE)

(72) Inventors: Konrad-Wenzel Winkler, Warin (DE); Inge Matthiesen, Behlendorf (DE)

(73) Assignee: HUMAN MED AG, Schwerin (DE)

( * ) Notice: Subject to any disclaimer, the term of this patent is extended or adjusted under 35 U.S.C. 154(b) by 442 days.

(21) Appl. No.: 13/915,125

(22) Filed: Jun. 11, 2013

(65) Prior Publication Data

US 2013/0344589 A1    Dec. 26, 2013

Related U.S. Application Data

(60) Provisional application No. 61/673,363, filed on Jul. 19, 2012.

(30) Foreign Application Priority Data

Jun. 22, 2012   (DE) .......................... 10 2012 210 653

(51) Int. Cl.
    *C12M 1/00*      (2006.01)
    *C12M 1/26*      (2006.01)

(52) U.S. Cl.
    CPC ............ *C12M 47/04* (2013.01); *C12M 33/14* (2013.01)

(58) Field of Classification Search
    CPC .............................. C12M 47/04; C12M 45/00
    USPC ....................................................... 435/309.1
    See application file for complete search history.

(56) References Cited

U.S. PATENT DOCUMENTS

| 3,384,354 | A  | * | 5/1968 | Migule et al. | 366/118 |
|---|---|---|---|---|---|
| 5,372,945 | A  | * | 12/1994 | Alchas et al. | 435/267 |
| 6,609,618 | B2 | * | 8/2003 | Colpan | 210/489 |
| 2002/0028431 | A1 | * | 3/2002 | Julien | C12Q 1/24 435/2 |
| 2005/0074436 | A1 |   | 4/2005 | Fraser et al. | |
| 2005/0084961 | A1 | * | 4/2005 | Hedrick et al. | 435/366 |
| 2006/0127875 | A1 | * | 6/2006 | Sukavaneshvar et al. | 435/2 |

(Continued)

FOREIGN PATENT DOCUMENTS

| DE | 10 2008 027 486 A  | 12/2009 |
|---|---|---|
| DE | 10 2011 080 218 A1 | 4/2012 |

(Continued)

OTHER PUBLICATIONS

European Search Report dated Aug. 21, 2013.

(Continued)

*Primary Examiner* — Liban M Hassan
(74) *Attorney, Agent, or Firm* — Norris McLaughlin, P.A.

(57) ABSTRACT

The invention relates to a device (100) for separating adult stem cells from adipose tissue taken from a biological structure. The device (100) has a container (110) for receiving a material mixture with the adipose tissue and the adult stem cells. Furthermore, the device (100) has a rinse agent feed device (120), a mixture feed device (130), a stem cell extraction device (140), a rinse agent drainage device (150), and a selectively permeable membrane (161-165). The container (110) has at least two chambers (171-174) which are separated from one another by at least one membrane (161-165). The mixture feed device (130) and the stem extraction device (140) are also separated by the at least one membrane (161-165).

12 Claims, 4 Drawing Sheets

(56) References Cited

U.S. PATENT DOCUMENTS

| | | | |
|---|---|---|---|
| 2006/0166307 A1* | 7/2006 | Detraz et al. | 435/41 |
| 2010/0112696 A1 | 5/2010 | Min | |
| 2010/0285521 A1* | 11/2010 | Vossman et al. | 435/379 |
| 2010/0285588 A1* | 11/2010 | Stubbers et al. | 435/379 |
| 2011/0294203 A1 | 12/2011 | Tsuchida | |
| 2012/0100611 A1 | 4/2012 | Kensy et al. | |

FOREIGN PATENT DOCUMENTS

| | | |
|---|---|---|
| EP | 2 371 943 A1 | 10/2011 |
| EP | 2 389 881 A1 | 11/2011 |
| JP | 2007-524396 A | 8/2007 |
| JP | 2009-38998 A | 2/2009 |
| JP | 2012-239458 A | 12/2012 |
| JP | 2015-500031 A | 1/2015 |
| WO | 2004/074457 A2 | 9/2004 |
| WO | 2006/127007 A2 | 11/2006 |
| WO | 2010/069080 A1 | 6/2010 |
| WO | 2010/073808 A1 | 7/2010 |
| WO | WO 2010135377 A1 * | 11/2010 |
| WO | 2011/079217 A1 | 6/2011 |
| WO | 2011/145075 A2 | 11/2011 |
| WO | 2013/030761 A1 | 3/2013 |
| WO | 2013/86199 A | 6/2013 |

OTHER PUBLICATIONS

German Search Report dated Mar. 12, 2015.
Japanese Office Action dated Feb. 17, 2015.
English Translation of Japanese Office Action dated Feb. 17, 2015.

* cited by examiner

DEVICE FOR SEPARATING ADULT STEM CELL

FIELD OF THE INVENTION

Background of the Invention

The present invention relates to a device for separating adult stem cells from adipose tissue taken from a biological structure.

It is known to obtain adipose tissue from biological structures, for example in human medicine. Adipose tissue can be extracted by using suitable suction devices and collected in so-called adipose cell collectors.

Description of the Related Art

It is known that the adipose tissue obtained in this way includes also stem cells in addition to fat cells. Stem cells are body cells that can differentiate into different cell types or tissues. The stem cells present in adipose tissue are so-called adult stem cells.

Obtaining such adult stem cells from adipose tissue is known, for example, from WO 2010/073 808 A1. The adipose tissue is hereby mixed with a fluid containing an enzyme, and the mixture is thereafter centrifuged in a container. This causes the stem cells to detach from the fat cells, so that they can be collected separately.

The separation can be effected by mechanical means, such as a fluid jet, as is known for example from DE 10 2011 080 218 A1.

SUMMARY OF THE INVENTION

According to the invention, a device for separating cells, preferably adult stem cells, from tissue, preferably adipose tissue, taken from a biological structure, preferably human or animal tissue, is provided.

The device includes a container, referred to also as stem cell collector, for receiving a material mixture, wherein the material mixture includes the tissue, preferably adipose tissue and cells, preferably the adult stem cells. The material mixture may also contain lipoaspirate or bone marrow.

Furthermore, the device includes at least one rinse agent feed device which is configured to introduce a fluid into the container. Preferably, the fluid includes an enzyme. Advantageously, a mechanical separation by an enzymatic digestion can thus be supported.

Likewise, the device includes a mixture feed device which is configured to introduce the material mixture into the container. The rinse agent feed device and the mixture feed device may represent one and the same opening in the container. Preferably, however, these feed devices are openings in the container that are different from one another and/or are spaced from one another.

The device also includes a stem cell extraction device, which is configured to remove the separated cells, preferably the separated stem cells, from the container. Advantageously, the stem extraction device may include a connector element for connecting a syringe which can be used to aspirate the cells.

Furthermore, the device includes at least one rinse agent drainage device configured to discharge from the container a mixture reduced by the adult stem cells. Preferably, the rinse agent is removed upon discharge from the container.

Advantageously, the rinse agent feed device, the mixture feed device, the stem cell extraction device and/or the rinse agent drainage device may each include a valve which is configured to pass a predeterminable quantity in a predeterminable time.

Advantageously, the stem cell suspension for the separation of enzymes, materials, proteins, blood components, and the like, can be optimally washed with an optional additional inlet port for a rinse solution, i.e. a rinse agent feed device, and an optional outlet port for the rinse solution, which is a rinse agent drainage device.

Preferably, each chamber has a corresponding rinse agent feed device and rinse agent drainage device to advantageously enable inside each chamber separate washing and discharging. Preferably, the rinse agent feed device and the rinse agent drainage device meet at one opening in one chamber.

Likewise, the device includes at least one selectively permeable membrane, also referred to as a filter, which is permeable to only a specific part of the respective material mixture. The at least one membrane may also be referred to as a filter assembly. An arrangement of a plurality of membranes can also be referred to as filter planes or as a filter group. The filter assembly includes at least a filter plane or filter group, preferably several filter planes or filter groups. The possibly individual successive filter planes or filter groups may in this case have a different pore size, passing only the stem cells and optionally gradually leaving behind, i.e. filtering out, larger particles which are bigger than the stem cells.

The membrane may also be a screen. Instead of the pore size, the screen has a hole size, which indicates the maximum particle size that can pass through the screen. An indication of the size of the pore size or hole size refers to a size equivalent diameter by a particle which just fits through the hole in the screen or through the pore of the membrane.

A pore size of the first membrane or a hole size of the first screen may be between 70 µm and 150 µm, preferably between 80 µm and 130 µm and more preferably between 90 µm and 110 µm.

A pore size of the second membrane or a hole size of the second screen may be between 20 µm and 65 µm, more preferably between 30 µm and 50 µm, and still more preferably between 35 µm and 45 µm.

A pore size of the third membrane or a hole size of the third screen may be between 5 µm and 65 µm, more preferably between 10 and 40 µm and still more preferably between 15 µm and 25 µm.

A membrane pore size of the fourth membrane or a hole size of the fourth screen may be between 1 µm and 30 µm, more preferably be between 2.5 µm and 22 µm and even more preferably between 5 µm and 15 µm.

The container has at least two chambers, also referred to as filter stages, which are separated from one another by at least one membrane, wherein the mixture feed device and stem cell extraction device are separated by at least one membrane. Such a chamber may also be called a filter plane. Preferably, an exchange of the rinse fluid and thus discharge of the filtered-out larger particles is possible in each filter plane. Preferably, new rinse fluid may be supplied, optionally simultaneously, to each filter plane by way of the rinse agent feed device. This is done, for example, by applying appropriate negative pressures to the appropriate chamber.

The filters in each filter plane can preferably be opened and closed. In this way, the timing of the start of filtering can be adjusted. Thus, washing of the stem cells from the remaining tissue cells or tissue cell residues can be optimized at each filter stage.

In a preferred embodiment of the invention, the at least two chambers have at least one pressure-equalizing valve which is designed to equalize pressure inside the container with pressure outside the container, and/or which is further adapted to repeatedly open and close.

Advantageously, an exposure time of, for example, enzymes or rinsing solutions can be determined separately for each chamber.

In another preferred embodiment of the invention, at least one of the at least two chambers includes a mechanically active element, which is configured to mix the fluid with the material mixture.

This advantageously decreases the time for obtaining the stem cells.

In addition, in a preferred embodiment of the invention, fluid can flow through the active element, which is furthermore configured so that a dynamic vacuum due to a flow velocity of the fluid suctions the material mixture toward the fluid, wherein the material mixture is accelerated in the direction of the flow velocity of the fluid.

Advantageously, the stem cells are separated from the adipose tissue cells by a fluid jet.

Preferably, the fluid jet is introduced at different pressures as a flat jet into the tissue stem cell mixture while closed off from the ambient air. The solution supplied via the fluid jet can also be discharged via a non-return valve.

Preferably, the active element has a Venturi nozzle, which has a capillary nozzle and an exit opening disposed in the direction of the jet at the capillary nozzle. The fluid may hereby flow into the chamber, suction the material mixture due to the dynamic vacuum and advantageously improve a mechanical separation and/or an enzymatic separation.

The active element may include an impact element which is arranged such that the accelerated material mixture strikes the impact element together with the flowing fluid.

This advantageously enables mechanical separation and improves intermixing with the rinse agent and/or improved wetting with the enzyme.

In a particularly preferred embodiment, the active element includes a stirring element, preferably a stirring pendulum, which is configured to perform a rotational movement similar to stirring and/or a rocking pendulum oscillation. The stirring element can be driven pneumatically, either by an overpressure and/or by a negative pressure.

Advantageously, the stirring element supports mechanical separation. The stem cells now detached from the tissue cells can be washed with a liquid, to which optionally enzymes have been added, and passed through a filter arrangement.

Preferably, the active element includes a non-stationary stamp piston, which is configured to displace the fluid with the mixture due to its spatial extent, and to repeatedly change its location of displacement. Advantageously, the resulting flow motion within the material mixture improves intermixing.

Oscillation of the stamp piston may also be excited pneumatically, especially by a vacuum.

According to another advantageous embodiment of the invention, the container includes a vibrator which is configured to excite oscillations in the fluid mixture. In this case, parts of the device or the device itself are subjected to a vibration, so that the separation of the stem cells from the tissue cells or from the tissue cell residues can be improved. In addition, the vibrator accelerates sedimentation of the stem cells in the material mixture. The vibrator may be connected to the at least one membrane for transmitting oscillations, for example, arranged below the membrane.

The vibrator may include a transducer such as a piezo element, a polarized film or a voice coil.

It is also conceivable to arrange a vibrator above the at least one membrane or to arrange the vibrator so that it can be guided over the at least one membrane. This vibration advantageously reduces clogging of the membrane.

Advantageously, the at least two chambers are directly connected with each other for fluid communication. This allows the mixture to move from one filter stage to the next filter stage.

The connection between the directly interconnected chambers may also have a valve which is configured to be repeatedly opened and closed. This allows a predefinable quantity of the mixture to move from one filter stage to the next filter stage at a predefinable time. This can also be referred to as opening and closing the filter, since a valve is arranged below at least one filter.

Preferably, the container has a temperature-control element configured to cool and/or heat the fluid and/or the material mixture. Preferably, the temperature-control element is arranged in a jacket of the container or in the jacket of the respective filter stage. The temperature-control element may include a Peltier element.

In a preferred embodiment of the invention, the spatial extent of the at least one membrane has the form of a cylindrical jacket, also referred to as a radial filter.

A pore size of the fifth membrane, i.e. of the radial filter, or a hole size of the fifth screen may be between 0.1 µm and 10 µm, more preferably between 0.3 µm and 5 µm and still more preferably between 0.5 µm and 3 µm.

Preferably, the last filter stage is designed as a radial filter stage. The vertically arranged radial filter advantageously results in an increased filter area in the last ultrafilter stage. The stem cells may precipitate, directly to the collection point (reservoir), without resting on the screen (without resting on the radial filter). This counters the risk that the stem cells attach themselves to or on the screen (on the radial filter).

After the last filter stage, the stem cell suspension can be removed from the system via a special discharge line. The pore size of the radial filter is hereby adjusted such that the stem cells remain inside the radial filter and the rinse fluid with the components to be washed out passes through the radial filter and is aspirated via the rinse solution outlet (the rinse agent drainage device), which is preferably under vacuum. The stem cells remain inside the radial filter and fall down into the reservoir due to gravity, from where the stem cells can then be removed separately.

Preferably, the at least one membrane has an electrostatic polarization. Advantageously, the membrane includes, at least partially, at least one electret or consists entirely of at least one electret. Possible electrets are, for example, polymers such as polytetrafluoroethylene, polytetrafluorethylenpropylen, polypropylene, polyethylene terephthalate, polyvinylidene fluoride, silicon dioxide or silicon nitride.

Advantageously, an identical electrostatic polarization between identical poles produces a repulsive force which prevents the mixture to be filtered and the particle passing through the filter or the membrane, respectively, from adhering to the membrane or the filter, respectively.

Preferably, the chamber may include a closed volume element, which may also be referred to as a solid body, with a volume of preferably at least 40%, more preferably of at least 50%, still more preferably of at least 60%, also preferably at least 70%, more preferably of at least 80% and still more preferably of at least 90% of a volume of the chamber. Preferably, oscillations in the volume element are excited by corresponding vibrating devices, for example by the vibrator. Advantageously, the stem cells can hereby be intermixed with and separated from the adipose tissue cells and the screen can then be cleaned.

To prevent damage to the fifth membrane resulting from an optionally alternating suction and pressurized rinse via the rinse agent discharge device, the fifth membrane is preferably supported in the direction of suction by a filter housing.

With the optional reverse pressure/pressurized rinse, the gap between the membrane and the volume element may be sized such that the fifth membrane is supported on the volume element.

Preferably, the filter housing and the closed volume element have radial slots. The slots are thus not continuous widened sections so as to attain optimal permeability of the fifth membrane. The slots are preferably effective when the fifth membrane is supported during the optional suction/pressurized rinse.

Advantageously, the solid body reduces the residual volume of the solution in which the stem cells reside, thus obviating the need for centrifugation.

Preferably, the container can be disassembled into separate components to facilitate cleaning of the components. The components may hereby include glass cylinders, the individual chambers, membranes, the radial filter, the valves, the vibrator, the temperature-control element and/or the active element.

BRIEF DESCRIPTION OF THE DRAWINGS

The invention will now be described in more detail with reference to the accompanying drawings which show in.

DETAILED DESCRIPTION OF THE INVENTION

Figure 1:
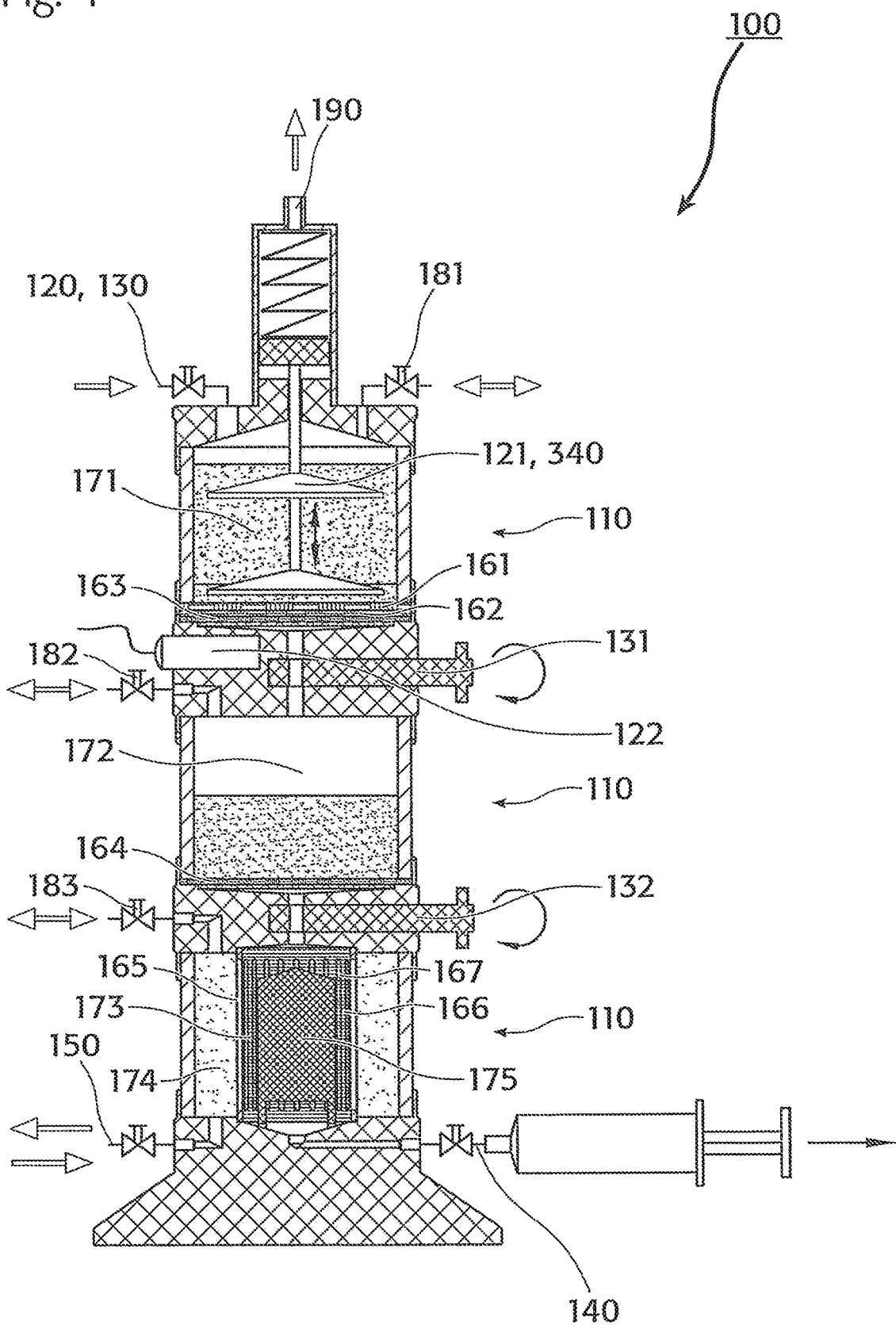
FIG. 1 a schematic diagram of a device for separating stem cells according to a first embodiment.

The same reference numeral is used for an element that corresponds in function and construction to an element of a previously referenced figure.

FIG. 1 shows a two-dimensional schematic diagram of a device generally designated as 100 for separating stem cells according to a first preferred embodiment. In this case, the device 100 has a container 110 which includes a first chamber 171, a second chamber 172 following in a flow direction, a third chamber 173 following in the flow direction, and a fourth chamber 174 following in the flow direction. The first chamber 171, the second chamber 172 and the fourth chamber 174 are each surrounded by a glass cylinder. The third chamber 173 is surrounded by a filter cylinder, also referred to as radial cylinder.

The first chamber 171 has in the lid a mixture feed device 130, as well as a rinse agent feed device 120, which in this illustration meet both in an opening of the lid. Furthermore, the cover has a first pressure equalization valve 181 that allows pressure equalization between an exterior and an interior of the container as well as a removal of rinse agent, enzymes and the material mixture reduced by the cells.

The first chamber 171 further includes an active element, in particular a vertically movable stamp piston 121. The stamp piston 121 may also be referred to as an impact element 340, since the fluid impinges thereon due to its movement. Due to the movement and the spatial extent of the stamp piston 121, the fluid with the material mixture is displaced, setting the flow in motion. The stamp piston 121 can be driven to oscillate, i.e. to perform a repeating up-and-down movement, pneumatically, for example by a pulsating negative pressure (vacuum 190), whereby a restoring force is provided by a spring element.

A first selectively permeable membrane 161 in the form of a first screen in direct contact with the mixture to be intermixed with the fluid is located at the bottom of the first chamber 171. The first membrane 161 has a hole size of 100 µm. A second selectively permeable membrane 162 (a second screen) follows in the direction of gravity and a third selectively permeable membrane 163 (a third screen), followed by a support screen.

To prevent adhesion of particles to the membranes, a vibrator 122 is disposed below the membranes and is connected with the membranes for transmitting vibrations.

The second chamber 172 follows below the first chamber 171 and below the first membrane 161 in the direction of gravity. The two chambers are fluidically connected to one another, wherein the connection includes a first valve 131 to determine the time when the material mixture flows from the first chamber 171 into the second chamber 172, or in other words, when the membranes (filters) open or close.

The second chamber 172 has likewise a pressure equalization valve, the second pressure equalization valve 182, which enables pressure equalization between an exterior and an interior of the container as well as removal of rinse agents, enzymes and the material mixture reduced by the cells. A membrane, the fourth selectively permeable membrane 164, i.e. the fourth membrane, is again located at the bottom of the second chamber 172. The fourth membrane 164 has a hole size of 10 µm.

The third chamber 173 follows below the second chamber 172 and below the fourth membrane 164 in the direction of gravity. The two chambers are fluidically connected to one another, wherein the connection includes a second valve 132 to determine the time when the material mixture flows from the second chamber 172 into the third chamber 173, or in other words, when the fourth membrane 164 (the fourth filter) opens or closes.

The third chamber 173 is surrounded on the side by a cylindrical membrane, the fifth selectively permeable membrane 165, also referred to as radial screen cylinder, radial cylinder or filter cylinder. The fifth membrane 165 has here a hole size of 1 µm.

The stem cells do not fit through this hole size. Therefore, the stem cells are collected in a reservoir having a capacity of approximately 5 ml for stem cells on the bottom of the third chamber 173, i.e. on the bottom inside the radial screen cylinder, and can therefrom be aspirated by a stem cell extraction device 140, which includes a valve and a connector for a syringe.

The fourth chamber 174 also includes a pressure equalization valve, the third pressure equalization valve 183, which enables pressure equalization between an exterior and an interior of the container. Likewise, the fourth chamber 174 has a rinse agent drainage device 150 which enables removal of rinse agents, enzymes and the material mixture reduced by the stem cells. An alternating suction and pressurized rinse on the rinse agent drainage device 150 prevents the stem cells from adhering on the radial filter membrane.

The third chamber 173 contains a closed volume element 175, which can be removed from the chamber 173, for example for cleaning purposes. The volume element 175 has about 70% to 90% of the volume of the chamber 173.

The volume element 175 has in the region facing the second valve 132 a curvature, so that the supplied material mixture meets the highest point of the volume element 175 and runs out from there toward the sides, i.e. the peripheral cylindrical surface of the volume element 175.

In order to keep the volume element 175 centered inside the third chamber 173 and prevent it from blocking the openings of the fifth membrane 165 while still providing enough space for the supplied material mixture as well as for the stem cells sliding down into the reservoir on the fifth membrane 165, the volume element 175 has in the respective upper and lower regions a non-continuous circumferential, radially protruding projection. Not circumferentially continuously means here that the annular projection does not form a closed ring round the volume element 175, but that the ring has instead indentations or recesses, in particular teeth disposed on its outer edge, i.e. the ring is outwardly serrated. The teeth may have various shapes, for example, similar to the shape of a fan rosette. Advantageously, the volume element 175 is thereby prevented from wobbling and rattling inside the third chamber 173.

To prevent damage to the fifth diaphragm 165 due to the alternating suction and pressurized rinse by the rinse agent drainage device 150, the fifth diaphragm 165 is supported by a filter housing 166 in the direction of suction.

During reverse pressure/pressurized rinsing, the gap between the membrane 165 and the volume element 175 is sized such that the membrane 165 is supported on the fifth volume element 175.

The filter housing 166 has radial slots 167 and the closed volume member 175 has radial, non-continuous projections for optimum permeability of the membrane 165, when the membrane 165 is supported during the suction/pressurized rinse.

The container 110 can largely be dismantled to facilitate cleaning.

To prevent the container 110 from tipping, it has a foot with a larger diameter compared to the rest of the cylindrical shape of the container 110 than the filter-functional part of the container 110.

Figure 2:
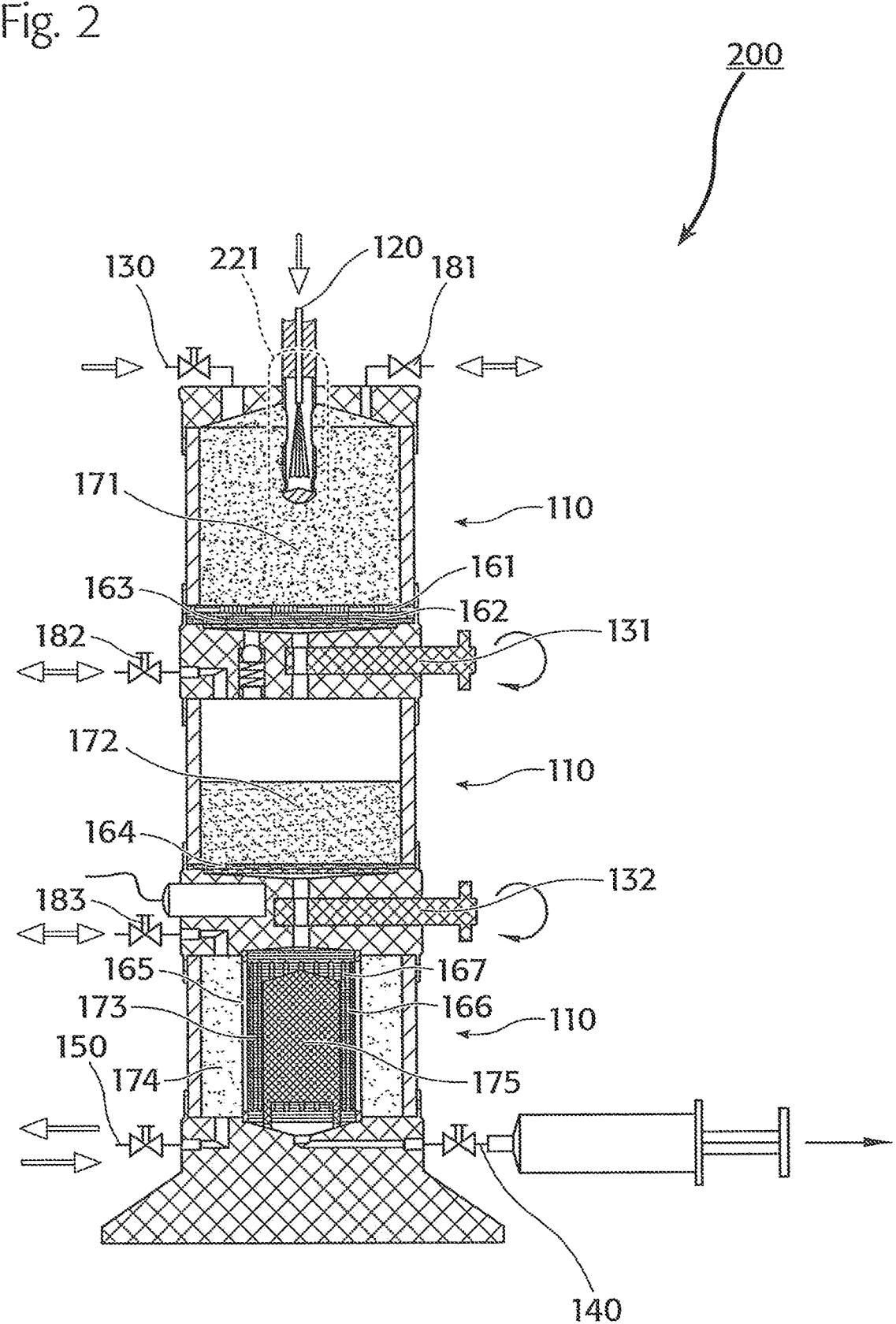
FIG. 2 a schematic diagram of a device for separating stem cells according to a second embodiment, and FIG. 3 a schematic diagram of an advantageous embodiment of a Venturi nozzle.

FIG. 2 shows a two-dimensional schematic diagram of a device generally designated with 200 for separating stem cells according to a second preferred embodiment.

The mixture feed device 130 located in the lid is separated and spaced apart from the rinse agent feed device 120 disposed in the lid. The rinse agent feed device 120 is combined with the active element, a Venturi nozzle 221, which opens into the first chamber 171.

Figure 3:
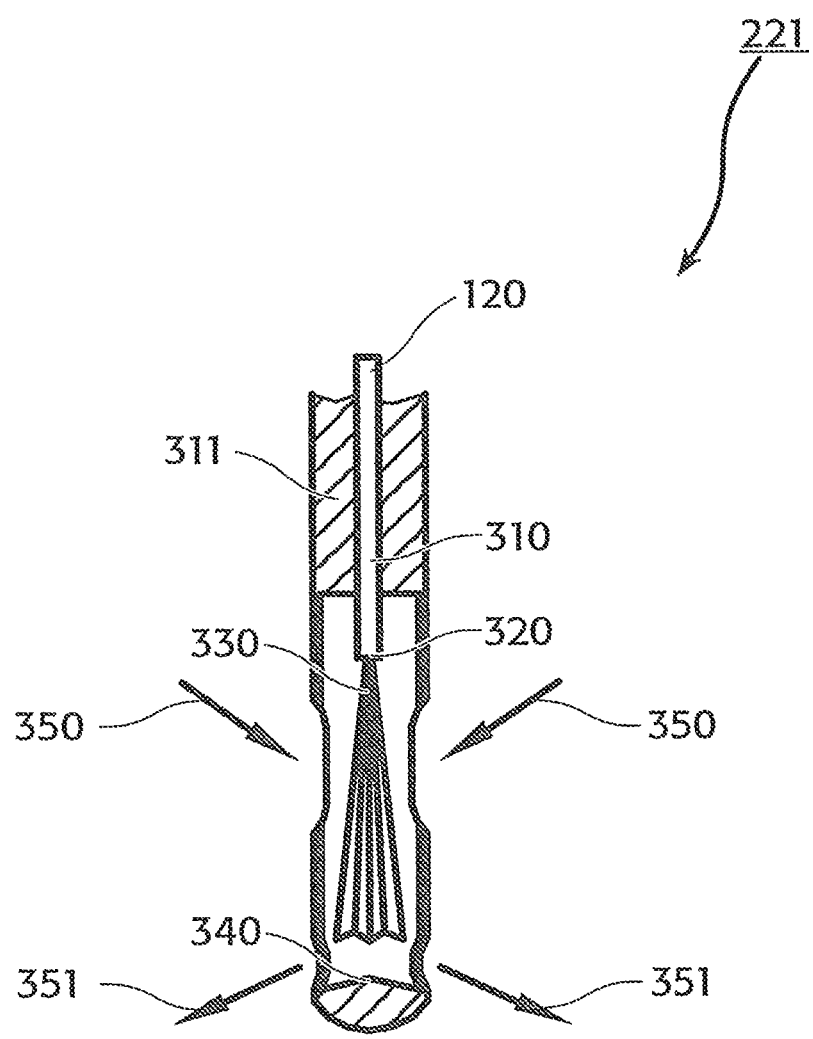
Figure 4:
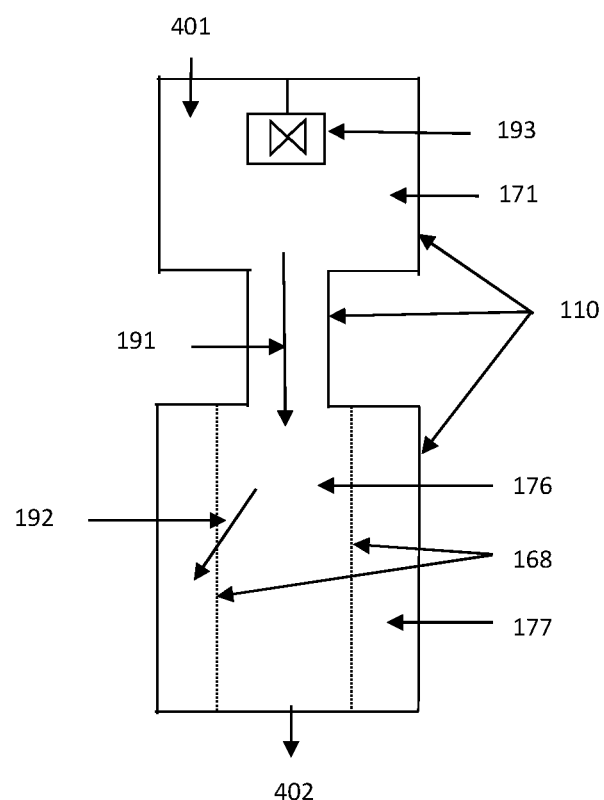
FIG. 4. A schematic diagram of a device for separating stem cells according to a further embodiment.

FIG. 3 shows a two-dimensional, enlarged schematic diagram of the Venturi nozzle generally indicated with 221, as an active element. The Venturi nozzle 221 includes hereby a cannula tube 311 with a capillary nozzle 310 disposed inside. The capillary nozzle 310 has an exit opening 320 in the direction of the jet, through which a fluid 330, in particular the rinse agent, can flow into the first chamber 171 at an elevated pressure. The material mixture, also referred to as tissue 350, is sucked in by the flow velocity of the fluid 330 and entrained by the jet. The entraining beam strikes an impact element 340. The tissue 350 is hereby intermixed with the rinse agent with the added enzyme and moves from the Venturi nozzle 221 as a tissue emulsion 351, i.e. better intermixed, to the first chamber 171.

LIST OF REFERENCE NUMERALS 100 first device for separating adult stem cells
110 container for receiving a material mixture
120 rinse agent feed device
121 stamp piston as the active element
122 vibrator
130 mixture feed device
131 first valve
132 second valve
140 stem cell extraction device
150 rinse agent drainage device
161 first selectively permeable membrane
162 second selectively permeable membrane
163 third selectively permeable membrane
164 fourth selectively permeable membrane
165 fifth selectively permeable membrane
166 filter housing
167 radial slots
168 final selectively permeable membrane
171 first chamber
172 second chamber
173 third chamber
174 fourth chamber
175 volume element
176 stem cell chamber
177 final chamber
181 first pressure equalization valve
182 second pressure equalization valve
183 third pressure equalization valve
190 vacuum
200 second device for separating adult stem cells
221 Venturi nozzle as active element
310 capillary nozzle
311 cannula tube
320 outlet opening
330 fluid
340 impact element
350 aspirated tissue
351 tissue emulsion
191 first flow path
192 final flow path
193 stirring pendulum
401 material mixture in
402 stem cell out

The invention claimed is:

1. A device for separating adult stem cells from adipose tissue taken from a biological structure, comprising:
   a container comprising a first chamber, a stem cell chamber and a final chamber, wherein all chambers are fluidly connected in sequence, the first chamber being located above both the stem cell chamber and the final chamber;
   the first chamber comprising at least one inlet port for introducing a fluid and a material mixture comprising adipose tissue and adult stem cells;
   the stem cell chamber comprising a stem cell outlet port;
   the final chamber comprising at least one final chamber outlet port;
   the container comprising an active element coupled to the first chamber, the active element configured to mix the fluid and the material mixture;

at least a first selectively permeable membrane having a first pore size and being located at a bottom of the first chamber, and between the first chamber and the stem cell chamber;

a final selectively permeable membrane having a final pore size and being located between the stem cell chamber and the final chamber, wherein the first pore size is larger than the final pore size which measures from 0.1 µm to 10 µm and the final selectively permeable membrane includes a cylindrical filter being arranged inside the final chamber, thereby forming the stem cell chamber inside the cylindrical filter, and the final chamber is defined between an outer surface of the cylindrical filter and an inner surface of the container, with a closed solid body located inside the cylindrical filter, having a volume of at least 40% of a volume of the cylindrical filter.

2. The device of claim 1, wherein each of the first chamber and the final chamber comprises a pressure equalization valve, adapted to selectively open and close a pressure equalization connection between the respective chamber and an exterior of the container.

3. The device according to claim 1, wherein the first chamber comprises a stirring pendulum as the active element, which is configured to perform a stirring rotational movement and/or a swing-type pendulum motion.

4. The device according to claim 1, wherein the first chamber comprises a non-stationary stamp piston as the active element which is configured to repeatedly change its location of displacement.

5. The device of claim 4, wherein the non-stationary stamp piston can be driven to oscillate by a vacuum.

6. The device according to claim 1, wherein the first chamber comprises a vibrator which is configured to introduce oscillations to an interior of the first chamber.

7. The device according to claim 2, wherein the at least one final chamber outlet port is configured so as to ensure an alternating suction and pressurized rinse.

8. The device according to claim 1, wherein the container comprises a temperature-control element which is configured to cool and/or heat an interior of the container.

9. The device according to claim 1, wherein the final selectively permeable membrane has an electrostatic polarization.

10. The device according to claim 1, wherein the first chamber comprises a Venturi nozzle as the active element, the Venturi nozzle extending from an exterior of the container to an interior of the first chamber with the Venturi nozzle forming an additional inlet port to the first chamber.

11. The device according to claim 10, wherein the Venturi nozzle comprises an exit opening and an impact element being disposed inside the first chamber, with the impact element physically connected to the Venturi nozzle and spaced apart from the exit opening.

12. A device for separating adult stem cells from adipose tissue taken from a biological structure, comprising:

a container comprising a first chamber, a second chamber, a stem cell chamber and a final chamber, wherein all chambers are fluidly connected in sequence, the first chamber being located above both the stem cell chamber and the final chamber;

the first chamber comprising at least one inlet port for introducing a fluid and a material mixture comprising adipose tissue and adult stem cells;

the stem cell chamber comprising a stem cell outlet port;

the final chamber comprising at least one final chamber outlet port;

the container comprising an active element coupled to the first chamber, the active element configured to mix the fluid and the material mixture at least a first selectively permeable membrane having a first pore size and being located at the bottom of the first chamber, and between the first chamber and the second chamber;

at least a second selectively permeable membrane having a second pore size and being located between the second chamber and the stem cell chamber;

a final selectively permeable membrane having a final pore size and being located between the stem cell chamber and the final chamber, wherein the first pore size is larger than the second pore size and the second pore size is larger than the final pore size which measures from 0.1 µm to 10 µm and wherein the final selectively permeable membrane includes a cylindrical filter being arranged inside the final chamber, thereby forming the stem cell chamber inside the cylindrical filter, and the final chamber is defined between an outer surface of the cylindrical filter and an inner surface of the container, with a closed solid body located inside the cylindrical filter, having a volume of at least 40% of a volume of the cylindrical filter.

* * * * *